US008470765B2

(12) United States Patent
Gemba et al.

(10) Patent No.: US 8,470,765 B2
(45) Date of Patent: Jun. 25, 2013

(54) POLYPEPTIDES AND ANTIBACTERIAL OR ANTISEPTIC USE OF SAME

(75) Inventors: Takefumi Gemba, Kawanishi (JP); Hideki Tomioka, Minoh (JP); Nao Tamura, Suita (JP); Akiko Tenma, Suita (JP)

(73) Assignee: AnGes MG, Inc., Osaka (JP)

( * ) Notice: Subject to any disclaimer, the term of this patent is extended or adjusted under 35 U.S.C. 154(b) by 0 days.

(21) Appl. No.: 13/254,843

(22) PCT Filed: Mar. 5, 2010

(86) PCT No.: PCT/JP2010/053618
§ 371 (c)(1),
(2), (4) Date: Nov. 15, 2011

(87) PCT Pub. No.: WO2010/101237
PCT Pub. Date: Sep. 10, 2010

(65) Prior Publication Data
US 2012/0052104 A1  Mar. 1, 2012

(30) Foreign Application Priority Data

Mar. 6, 2009  (JP) ................................ 2009-053408

(51) Int. Cl.
*C07K 7/08* (2006.01)
(52) U.S. Cl.
USPC ............... 514/1.1; 514/2.2; 514/2.3; 514/2.4; 514/3.3
(58) Field of Classification Search
USPC ...................... 514/1.1, 2.2–2.4, 3.3
See application file for complete search history.

(56) References Cited

U.S. PATENT DOCUMENTS

| 7,452,856 | B2 | 11/2008 | Nagaoka et al. |
| 7,674,771 | B2 | 3/2010 | Yoshida et al. |
| 7,807,176 | B2 | 10/2010 | Nishikawa et al. |
| 7,964,556 | B1 | 6/2011 | Kobayashi et al. |
| 8,012,749 | B2 | 9/2011 | Yano et al. |
| 2005/0214321 | A1 | 9/2005 | Rasochova et al. |
| 2006/0122122 | A1 | 6/2006 | Kobayashi et al. |
| 2007/0032431 | A1 | 2/2007 | Yoshida et al. |
| 2007/0281888 | A1 | 12/2007 | Nishikawa et al. |
| 2008/0025962 | A1 | 1/2008 | Hayashi et al. |
| 2008/0069849 | A1 | 3/2008 | Schmidtchen et al. |
| 2009/0143319 | A1 | 6/2009 | Gemba et al. |
| 2009/0149632 | A1 | 6/2009 | Nagaoka et al. |
| 2010/0167390 | A1 | 7/2010 | Nakajima et al. |
| 2012/0122766 | A1 | 5/2012 | Gemba et al. |
| 2012/0172287 | A1 | 7/2012 | Gemba et al. |

FOREIGN PATENT DOCUMENTS

| EP | 2 371 840 A1 | 10/2011 |
| EP | 2 436 688 A1 | 4/2012 |
| JP | 2006-45214 | 2/2006 |
| JP | 2006-160640 | 6/2006 |
| JP | 2007-512842 | 5/2007 |
| WO | WO 01/12668 A1 | 2/2001 |
| WO | WO 2005/049819 | 6/2005 |
| WO | WO 2005/090564 | 9/2005 |
| WO | WO 2006/054947 | 9/2006 |
| WO | WO 2008/096814 | 8/2008 |
| WO | WO 2008/096816 | 8/2008 |
| WO | WO 2010/061915 | 6/2010 |
| WO | WO 2010/137594 | 12/2010 |

OTHER PUBLICATIONS

UniProtKB/TrEMBL Protein Accession No. C0PK96 at http://www.uniprot.org/uniprot/C0PK96, accessed Sep. 4, 2012.*
International Search Report for PCT/JP2010/053618 filed Mar. 5, 2010.
International Preliminary Report on Patentability for PCT/JP2010/053618 filed Mar. 5, 2010.
Written Opinion of the International Searching Authority for PCT/JP2010/053618 filed Mar. 5, 2010.
International Search Report for PCT/JP2010/058838 filed May 25, 2010, (counterpart of co-pending U.S. Appl. No. 13/322,424).
International Preliminary Report on Patentability for PCT/JP2010/058838 filed May 25, 2010, (counterpart of co-pending U.S. Appl. No. 13/322,424).
Written Opinion of the International Searching Authority for PCT/JP2010/058838 filed May 25, 2010, (counterpart of co-pending U.S. Appl. No. 13/322,424).
International Search Report for PCT/JP2009070035 filed Nov. 27, 2009, (counterpart of co-pending U.S. Appl. No. 13/131,796).
International Preliminary Report on Patentability for PCT/JP2009070035 filed Nov. 27, 2009, (counterpart of co-pending U.S. Appl. No. 13/131,796).
Written Opinion of the International Searching Authority for PCT/JP2009070035 filed Nov. 27, 2009, (counterpart of co-pending U.S. Appl. No. 13/131,796).
Extended European Search Report for EP 09829160.2 (counterpart of co-pending U.S. Appl. No. 13/131,796).
English language abstract for WO 2008/096814, listed as document B7 above.
English language abstract for WO 2008/096816, listed as document B8 above.
Aurora, et al., "Helix capping," *Protein Science* 7(1):21-38 (1998).
Brenneman, et al., "Protective Peptides That Are Orally Active and Mechanistically Nonchiral," *J. Pharmacol. Exp. Ther.* 309(3):1190-1197 (2004).

(Continued)

*Primary Examiner* — Christina Bradley
*Assistant Examiner* — Kristina M Hellman
(74) *Attorney, Agent, or Firm* — Law Office of: Michael A. Sanzo, LLC

(57) ABSTRACT

A novel polypeptide, and an antibacterial agent, antifungal agent and/or antiseptic containing as an effective ingredient the polypeptide are disclosed. The polypeptide of this invention has an amino acid sequence shown in SEQ ID NOs:1 to 12 and 13 to 31. This antibacterial agent, antifungal agent and/or antiseptic is useful for the prevention, amelioration or treatment of diseases such as burn, decubitus, wound, skin ulcer, leg ulcer, diabetic ulcer, occlusive arterial disease and arteriosclerosis obliterans, cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis).

19 Claims, No Drawings

OTHER PUBLICATIONS

D'Andrea, et al., "Targeting angiogenesis: Structural characterization and biological properties of a de novo engineered VEGF mimicking peptide," *Proc. Natl. Acad. Sci. USA* 102(40):14215-14220 (Oct. 4, 2005).

Dharap, et al., "Tumor-specific targeting of an anticancer drug delivery system by LHRH peptide," *Proc. Natl. Acad. Sci. USA* 102(36):12962-12967 (Sep. 6, 2005).

Hayward, et al., "Fibroblast growth factor reverses the bacterial retardation of wound contraction," *Am. J. Surg.* 163(3):288-293 (Mar. 1992).

Herouy, et al., "Matrix metalloproteinases and venous leg ulceration," *Eur. J. Dermat.* 10(3):173-180 (2000).

Koczulla, et al., "An angiogenic role for the human peptide antibiotic LL-37/hCAP-18," *J. Clin. Invest.* 111(11):1665-1672 (Jun. 2003).

López-Garcia, et al., "Anti-Fungal Activity of Cathelicidins and their Potential Role in *Candida albicans* Skin Infection," *J. Invest. Dermatol.* 125(1):108-115 92005).

Martinez, et al., "Proadrenomedullin $NH_2$-Terminal 20 Peptide Is a Potent Angiogenic Factor, and Its Inhibition Results in Reduction of Tumor Growth," *Cancer Res.* 64(18):6489-6494 (Sep. 15, 2004).

Nakagami, et al., "Anti-microbial Peptide and angiogenesis," *J. Jpn. Coll. Angiol.* 48:437-440 (2008).

Sato, et al., "Glycoinsulins: Dendritic Sialyloligosaccharide-Displaying Insulins Showing a Prolonged Blood-Sugar-Lowering Activity," *J. Am. Chem. Soc.* 126(43):14013-14022 (2004).

Sato, et al., "Site-Specific Introduction of Sialic Acid into Insulin," *Angew. Chem. Int. Ed.* 43(12):1516-1520 (2004).

Shinoyama, et al., "Cutaneous Ulceration," *Japanese Journal of Clinical Dialysis* 24(7):819-821 (2008) with translation of title and first paragraph attached.

Sawai, et al., "Impact of single-residue mutations on the structure and function of ovispirin/novispirin antimicrobial peptides," *Protein Eng.* 15(3):225-232 (2002).

Stenberg, et al., "Effect of bFGH on the inhibition of contraction caused by bacteria," *J. Surg. Res.* 50(1):47-50 (1991).

Ulbricht, et al., "The Use of PEG-Hirudin in chronic hemo-dialysis monitored by the Ecarin Clotting Time: influence on clotting of the extracorporeal system and hemostatic parameters," *Clin. Nephrol.* 65(3):180-190 (2006).

Wilkemeyer, et al., "Ethanol Antagonist Peptides: Structural Specificity without Stereospecificity," *J. Pharmacol. Exp. Ther.* 309(3):1183-1189 (2004).

Zanetti, et al., "Cathelicidins multifunctional peptides of the innate immunity," *J. Leukoc. Biol.* 75(1):39-48 (Jan. 2004).

Zasloff, et al., "Magainins, a class of antimicrobial peptides from *Xenopus* skin: Isolation, characterization of two active forms, and partial cDNA sequence of a precursor," *Proc. Natl. Acad. Sci. USA* 84(15):5449-5453 (Aug. 1987).

English translation of Shinoyama, et al., "Cutaneous Ulceration," *Japanese Journal of Clinical Dialysis* 24(7):819-821 (2008).

European Search Report for Europeon patent office Application EP 10 78 0549 (which is a counterpart of copending U.S. Appl. No. 13/322,424) prepared Dec. 6, 2012 and mailed Dec. 18, 2012.

Nakagami, et al., "Modification of a novel angiogenic peptide, AG30, for the development of novel therapeutic agents," *J. Cell. Mol. Med.* 16(7):1629-1639 (Jun. 2012).

Nishikawa, et al., "Development of a novel antimicrobial peptide, AG-30, with angiogenic properties," *J. Cell. Mol. Med.* 13(3):535-546 (Mar. 2009).

Nishikawa, et al., "Analysis of De Nova Engineered Variants of AG-30 for the Treatment of Ischemic Diseases and Infectious Diseases," abstract from the 14th Annual Meeting of the Japan Society of Gene Therapy (Jun. 12-14, 2008), Abstract No. 37, published in *J. Gene Med.* 11:1138-1190, see pp. 1166-1167 (Dec. 2009).

* cited by examiner

POLYPEPTIDES AND ANTIBACTERIAL OR ANTISEPTIC USE OF SAME

CROSS REFERENCE TO RELATED APPLICATIONS

The present application is US national stage of international application, PCT/JP2010/053618 which had an international filing date of Mar. 5, 2010, and which was published in Japanese under PCT Article 21(2) on Sep. 10, 2010. Priority is claimed to Japanese application JP 2009-053408, filed on Mar. 6, 2009.

TECHNICAL FIELD

The present invention relates to a novel polypeptide and its use as an antibacterial, antifungal and/or antiseptic.

BACKGROUND ART

As a type of antibacterial agents, polypeptide-based antibacterial agents comprising a polypeptide are known. Polypeptide-based antibacterial agents exhibit a wide antibacterial spectrum and some of them are known to exhibit antibacterial activity against bacteria resistant to other types of antibiotics. Examples thereof include magainin (Non-Patent Document 1), cathelicidin (LL-37) (Non-Patent Document 2) and Ovispirin-1 (Non-Patent Document 3) which are α helix antibacterial peptides. In addition to these, peptides having an antibacterial activity, such as defensins (Non-Patent Document 2) are known. Further, in recent years, novel α helix antibacterial peptides are created (Patent Document 1). However, their antibacterial activities are not sufficient when compared with those of the existing antibiotics. Thus, novel polypeptide-based antibacterial agents having a novel structure and an excellent antibacterial activity are continuously demanded.

Patent Document 2 suggests that polypeptides having a vascular endothelial growth activity also have an antibacterial activity. Patent Document 3 describes analogues of the polypeptides described in Patent Document 2, which have a particularly high antibacterial activity.

PRIOR ART DOCUMENTS

Patent Documents

Patent Document 1; JP 2006-45214 A
Patent Document 2: WO 2005/090564 A1
Patent Document 3: WO 2008/096814 A1

Non-Patent Documents

Non-patent Document 1: Proc Natl Acad Sci USA., 1987 August; 84(15):5449-53,
Non-patent Document 2: J Invest Dermatol., 2005 July; 125 (1):108-115,
Non-patent Document 3: Protein Eng., 2002 March; 15(3): 225-232.

SUMMARY OF THE INVENTION

Problems to be Solved by the Invention

An object of the present invention is to provide a novel polypeptide having an excellent antibacterial activity, and antibacterial agent, antifungal agent and/or antiseptic comprising the polypeptide as an effective ingredient.

Means for Solving the Problems

The present inventors intensively studied to discover that by modifying the polypeptides described in Patent Documents 2 and 3, polypeptides having a higher antibacterial activity than these polypeptides are obtained, thereby completing the present invention.

That is, the present invention provides the following:
(1) A polypeptide whose amino acid sequence is shown in any one of SEQ ID NOs:1 to 12 and 13 to 31,
(2) The polypeptide according to (1), whose carboxyl-terminal is amidated.
(3) The polypeptide according to (1) or (2), whose amino-terminal is acetylated.
(4) An antibacterial agent, antifungal agent and/or antiseptic comprising as an effective ingredient said polypeptide according to any one of (1) to (3).
(5) The polypeptide according to any one of (1) to (3) for use in an antibacterial agent, antifungal agent and/or antiseptic.
(6) An article for antiseptic, antibacterial and/or antifungal, comprising a base material coated with and/or impregnating said polypeptide according to any one of (1) to (3).
(7) The article for antiseptic, antibacterial and/or antifungal according to (6), wherein said base material is a gauze, bandage, cotton, woven fabric, non-woven fabric, knit, knitted fabric, compression sheet, or compression fabric or paper.
(8) A drug spray, cotton or spray for disinfection of fingers, antibacterial and/or antifungal solution for medical instruments, comprising said polypeptide according to any one of (1) to (3).
(9) An agent for prevention, amelioration or treatment of a disease(s) selected from the group consisting of burn, decubitus, wound, skin ulcer, leg ulcer, diabetic ulcer, occlusive arterial disease and arteriosclerosis obliterans cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis), said agent comprising as an effective ingredient said polypeptide according to any one of (1) to (3).
(10) A method for prevention, amelioration or treatment of a disease(s) selected from the group consisting of burn, decubitus, wound, skin ulcer, leg ulcer, diabetic ulcer, occlusive arterial disease and arteriosclerosis obliterans, cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis), said method comprising administering to a mammal said polypeptide according to any one of (1) to (3).
(11) The polypeptide according to any one of (1) to (3) for use in prevention, amelioration or treatment of a disease(s) selected from the group consisting of burn, decubitus, wound, skin ulcer, leg ulcer, diabetic ulcer, occlusive arterial disease and arteriosclerosis obliterans, cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis).

Effects of the Invention

By the present invention, novel polypeptides having an excellent antibacterial activity and/or antifungal activity, as well as antibacterial agents, antifungal agents and/or antiseptics comprising as an effective ingredient the polypeptide were provided.

Further, by the present invention, agents for prevention, amelioration or treatment of a disease(s) selected from the group consisting of burn, decubitus, wound, skin ulcer, leg ulcer, diabetic ulcer, occlusive arterial disease and arteriosclerosis obliterans, cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis), the agent comprising as an effective ingredient the polypeptide, were provided.

MODE FOR CARRYING OUT THE INVENTION

In the present Description, the terms "polypeptide" and "peptide" have the same meaning.

The amino acid sequence of Ovispirin-1 (also called as AP00196, see http://aps.unmc.edu/AP/main.php) described in Non-Patent Document 3 is shown in SEQ ID NO:12. As will be concretely described in the Examples below, Ovispirin-1 has an antibacterial activity. Using Ovispirin-1 as a positive control, the antibacterial activity of the polypeptides of the present invention was examined. As a result, it was proved that the above-described polypeptides of the present invention have an excellent antibacterial activity.

The polypeptide of the preset invention may be modified at the amino-terminal (N-terminal) and/or carboxyl-terminal (C-terminal) thereof. In some cases, it may be preferred that the C-terminal be amidated and the N-terminal be acetylated. A capping structure may be added to the polypeptide of the present invention. The capping structure is an oligopeptide attached to the N-terminal and/or C-terminal of a polypeptide, which is known to stabilize the structure of the polypeptide (Document: 1) D'Andrea L D, Iaecarino U, Fattorusso R, Sorriento D, Carannante C, Capasso D, Trimarco B, Pedone C., "Targeting angiogenesis: structural characterization and biological properties of a de novo engineered VEGF mimicking peptide.", Proc Natl Acad Sci USA., 2005 Oct. 4; 102(40): 14215-20, Epub 2005 Sep. 26; 2) (Document: 2) Aurora R, Rose G D., "helix capping"., Protein Sci, 1998 January; 7(1): 21-38).

In general, with respect to a pharmaceutical composed of a polypeptide(s), techniques to increase the stability of the polypeptide(s) in vivo, wherein a sugar chain(s) and/or a polyethylene glycol (PEG) chain(s) is(are) added to the polypeptide(s), or wherein a D-amino acid(s) is(are) used as at least one part of the amino acids constituting the polypeptide(s), are widely known and used. The addition of a sugar chain(s) and/or a PEG chain(s) to a polypeptide, or the use of a D-amino acid(s) as at least one part of the amino acids constituting a polypeptide makes the polypeptide more unlikely to be decomposed by a peptidase(s) in vivo, and in turn, makes the half-life of the polypeptide in vivo longer. The polypeptides of the present invention may be polypeptides which are modified with these known modifications for the stabilization in vivo, as long as they have an antibacterial activity. And, the term "polypeptide" as used herein and in the appended claims includes polypeptides which are modified with a modification(s) for the stabilization in vivo, unless the context clearly dictates otherwise.

The addition of a sugar chain to a polypeptide is well-known, and described, for example, in Sato M, Furuike T, Sadamoto R, Fujitani N, Nakahara T, Niikura K, Monde K, Kondo H, Nishimura S., "Glycoinsulins: dendritic sialyloligosaccharide-displaying insulins showing a prolonged blood-sugar-lowering activity.", J Am Chem. Soc. 2004 Nov. 3; 126(43):14013-22, and Sato M, Sadamoto R, Niikura K, Monde K, Kondo H, Nishimura S, "Site-specific introduction of sialic acid into insulin.", Angew Chem Int Ed Engl. 2004 Mar. 12; 43(12):1516-20. A sugar chain can be bound to N-terminus. C-terminus or the amino acid therebetween, but it is preferred that a sugar chain be bound to N-terminus or C-terminus, in order not to inhibit the activity of the polypeptide. The number of the sugar chains is preferably one or two, more preferably one. The sugar chain is preferably from mono- to tetra-saccharide, more preferably disaccharide or trisaccharide. The sugar chain(s) can be bound directly to a free amino group(s) or a carboxyl group(s) on the polypeptide, or through a spacer structure(s) such as a methylene chain whose number of carbon atoms is about 1 to 10.

The addition of a PEG chain to a polypeptide is also well-known, and described, for example, in Ulbricht K, Bucha E, Posehel K A, Stein G, Wolf G, Nowak G., "The use of PEG-Hirudin in chronic hemodialysis monitored by the Ecarin Clotting Time; influence on clotting of the extracorporeal system and hemostatic parameters.", Clin Nephrol. 2006 March; 65(3):180-90, and Dharap S S, Wang Y, Chandna P, Khandare J J, Qiu B, Gunaseelan S, Sinko P J, Stein S, Farmanfarmaian A, Minko T., "Tumor-specific targeting of an anticancer drug delivery system by LHRH peptide.", Proc Natl Acad Sci USA. 2005 Sep. 6; 102(36):12962-7. A PEG chain can be bound to N-terminus, C-terminus or the amino acid therebetween, and one or two PEG chains are usually bound to a free amino group(s) and/or carboxyl group(s) on the polypeptide. The molecular weight of the PEG chain is not particularly limited, but typically about 3000 to 7000, preferably about 5000.

The method the changing at least one part of the amino acids constituting the polypeptide into D-isomer is also well-known, and described, for example, in Brenneman D E, Spong C Y, Hauser J M, Abebe D, Pinhasov A, Golian T, Gozes I., "Protective peptides that are orally active and mechanistically nonchiral", J Pharmacol Exp Then 2004 June; 309(3):1190-7, and Wilkemeyer M F, Chen S Y, Menkari C E, Sulik K K, Charness M E., "Ethanol antagonist peptides: structural specificity without stereospecificity.", J Pharmacol Exp Ther. 2004 June; 309(3):1183-9. At least one part of the amino acids constituting the polypeptide may be a D-amino acid(s), but it is preferred that all of the amino acids constituting the polypeptide be D-amino acids, in order to inhibit the activity of the polypeptide as little as possible.

The polypeptides of the present invention can easily be produced by a conventional method such as chemical synthesis using a commercially available peptide synthesizer. Further, the above-described modifications for stabilization can also be easily carried out by the well-known methods as described in the above-described references.

Since the polypeptides of the present invention have an antibacterial activity and/or antifungal activity, they may be used as an antibacterial agent, antifungal agent and/or antiseptic. How to use the polypeptide as an antibacterial agent, antifungal agent and/or antiseptic is the same as the known polypeptide-based antibacterial agents and/or antifungal agents, and may preferably be administered in the form of an ointment, aqueous solution, powder, gel or percutaneous patch, especially preferably in the form of an ointment. The methods of formulation to these formulations are well-known, and any of the well-known methods may be employed. The concentration of the polypeptide in the ointment is not restricted, and is usually about 0.1 mg/g to 100 mg/g, especially about 1 mg/g to 10 mg/g. The concentration of the polypeptide in the solution is not restricted, and is usually about 0.1 mg/mL to 100 mg/mL, especially about 1 mg/mL to 10 mg/mL. The administration route may be topical administration such as application or injection to the site where the antibacterial and/or antiseptic action is/are needed; systemic parenteral administration such as intravenous injection; or oral administration. Topical administration and systemic parenteral administration are preferred, especially topical administration is preferred. The application is not limited to a living body, but the polypeptide may be used for sterilization or disinfection of articles. The dose of administration when the polypeptide is administered to a living body is appropriately selected depending on the symptom or the size of the diseased portion, and usually about 0.1 mg to 100 mg, especially about 1 mg to 10 mg in terms of the amount of the polypeptide. However, needless to say, the dose is not limited to these ranges.

In cases where the polypeptide of the present invention is formulated into an antibacterial agent, antifungal agent and/or antiseptic, the form of formulation is not limited, and may be formulated into the form of, for example, solution, suspension, gel, paste or solid.

In cases where the polypeptide of the present invention is coated or impregnated, preferred examples of the base material therefor include gauze, bandage, cotton, woven fabric, non-woven fabric, knit, knitted fabric, compressed sheet and compression fabric or paper. These materials may be used individually or in combination.

The polypeptide of the present invention may be formulated into the form of a solution, and may be used as a drug spray (powder or mist), cotton or spray for disinfection of fingers or antibacterial and/or antifungal solution for medical instruments. Further, the polypeptide of the present invention formulated into the form of a solution may be incorporated in eye drops.

Specific examples of the diseases and disorders when the polypeptide is administered to a living body include, but are not limited to, burn, decubitus (bedsore), wound, skin ulcer, leg ulcer, diabetic ulcer, occlusive arterial disease and arteriosclerosis obliterans, cellulitis, acute lymphangitis, lymphadenitis, erysipelas, skin abscess, necrotizing subcutaneous infection, staphylococcal scalded skin syndrome (SSSS), folliculitis, facial furuncle, suppurative hidradenitis, carbuncle, infectious paronychia, erythrasma and severe infection (sepsis). The antibacterial agent and/or antiseptic of the present invention may be used as an antibacterial agent, antifungal agent and/or antiseptic against these diseases or disorders.

The antibacterial agent, antifungal agent and/or antiseptic may be used individually, or together with other antibacterial agent(s), antifungal agent(s) and/or antibiotic(s). Examples of these antibacterial agents, antifungal agents and antibiotics include, but are not limited to, cephem antibiotics, carbapenem antibiotics, aminoglycoside antibiotics, new quinolone antibiotics, β-lactam antibiotics, penicillin antibiotics and glycopeptide antibiotics, more specifically, ceftazidime, meropenem, tobramycin, ciprofloxacin, methicillin, ampicillin and vancomycin.

The polypeptide of the present invention may be used as an antibacterial agent, antifungal agent and an antiseptic. In cases where at least two of the antibacterial action, antifungal action and disinfection action are desired, the agent may be used as an agent which simultaneously attain at least two of these activities. For example, in cases where the antibacterial activity and disinfection activity are desired, the polypeptide may be used as an antibacterial agent and antiseptic. That is, although the term "mataha" has the both meanings of "at least one" and "only one of them" (IWANAMI SHOTEN, KOJIEN 4th edition), in the present Description and in the claims, the term is used for expressing the former meaning unless the context clearly dictates otherwise. In this case, the corresponding English word is "and/or".

The present invention will now be described more concretely by way of Examples thereof. However, the present invention is not restricted to the Examples below.

EXAMPLES

1. Synthesis of Polypeptides

Protected peptide resins were synthesized by Fmoc method using a full-automatic solid-phase synthesizer according to the method described in documents such as Solid Phase Peptide Synthesis, Pierce (1984), Fmoc solid synthesis: a practical approach, Oxford University Press (2000) and The Fifth Series of Experimental Chemistry, Vol. 16, Synthesis of Organic Compounds IV. To the obtained protected peptide resins, trifluoroacetic acid (TFA) and a scavenger (a mixture of thioanisole, ethanedithiol, phenol, triisopropylsilane, water, etc.) were added to obtain crude peptides by cleaving from the resin and deprotecting. These crude peptides were purified by gradient elution using a reversed-phase HPLC column (ODS) in 0.1% TFA-$H_2O$/$CH_3CN$ system. Fractions containing the desired substances were collected and freeze-dried to obtain the desired peptides.

The amino acid sequences of the synthesized peptides were confirmed by using an amino acid sequencer G1000A (Hewlett Packard), PPSQ-23A (SHIMADZU CORPORATION) or ProciscLC (ABI).

The sequences of the synthesized polypeptides are shown below. In the present description, Ovispirin-1 used as the positive control is called Ovispirin-1. The C-termini of the polypeptides other than SRP-7 were amidated.

```
                                        (SEQ ID NO: 1)
SRP-7         IFLHRLKRMRKRLKRKLRLW (SEQ ID NO: 2)
SRP-8         RLKRMRKRLKRKLRLWHRKRYK-amide (SEQ ID NO: 3)
SRP-9         MLKLIFLHRLKRMRKRLKRKLR-amide (SEQ ID NO: 4)
SRP-10        MLKLIFLHRLKRMRKRLKRK-amide (SEQ ID NO: 5)
SRP-11        LKLIFLHRLKRMRKRLKRKL-amide (SEQ ID NO: 6)
SRP-12        LIFLHRLKRMRKRLKRKLRL-amide (SEQ ID NO: 7)
SRP-13        KLIFLHRLKRELRKRLKRKLR-amide (SEQ ID NO: 8)
SRP-14        GRLKRMGKRLKRKIQKWARW-amide (SEQ ID NO: 9)
SRP-15        GRLKRMGERLKRKIQKWIRW-amide (SEQ ID NO: 10)
SRP-16        KLIFLRELRRLRKRLKRKLR-amide (SEQ ID NO: 11)
SRP-17        RLKRMRKRLKRKLRLW-amide (SEQ ID NO: 12)
Ovispirin-1   KNLRRIIRKIIHIIKKYG-amide
```

2. Analysis of the Polypeptides Using MALDI-TOF/MS

The sequences of the synthesized polypeptides were confirmed by the results of analysis using MALDI-TOF/MS. To 1 μL, of a solution containing 0.1% polypeptide in TFA/50% acetonitrile, whose final concentration was 100 μg/mL, 1 μL, of a matrix solution (α-Cyano 4-Hydroxy Cinnamic Acid) was added to obtain a measurement sample for MALDI. The measurement sample for MALDI (0.4 μL) was applied on a MALDI target plate and dried, followed by measurement using MALDI-TOF/MS.

MALDI-TOF/MS Conditions:
 Laser intensity: 2100
 Number of shots: 1000

The theoretical value and measured value of MALDI-TOF/MS for each polypeptide are shown in Table 1. The detected m/z of each polypeptide was matched to each theoretical value, and the sequences of the synthesized polypeptides were confirmed.

TABLE 1

| | MH + (Da) | |
|---|---|---|
| Polypeptide | Theoretical value | Measured value |
| SRP-7 | 2747.756375 | 2747.7163 |
| SRP-8 | 3104.991295 | 3014.9700 |
| SRP-9 | 2932.912555 | 2932.8076 |
| SRP-10 | 2663.727385 | 2663.7898 |
| SRP-11 | 2645.770955 | 2645.8450 |
| SRP-12 | 2673.777105 | 2673.8452 |
| SRP-13 | 2799.874165 | 2799.9692 |
| SRP-14 | 2594.604625 | 2594.7422 |
| SRP-15 | 2637.599205 | 2637.8821 |
| SRP-16 | 2690.821405 | 2690.9329 |
| SRP-17 | 2236.476915 | 2236.5281 |
| Ovispirin-1 | 2261.492595 | 2261.5903 |

3. Antibacterial Activity of Polypeptides

The antibacterial activity of the polypeptides was measured using the ATP assay method.

Using BacTiter-Glo Microbial Cell Viability Assay kit available from PROMEGA, the antibacterial activity of the peptides was evaluated from the viability of bacteria. That is, ATP amount in viable bacteria in cases where the concentration of the peptides was 10 μg/ml, was measured using a microtiter plate or test tubes.

With respect to the strains, *Staphylococcus aureus* (*S. aureus* ATCC29213) as Gram-positive bacteria, or, alternatively, *Pseudomonas aeruginosa* (*P. aeruginosa* ATCC27853) as Gram-negative bacteria, was used. The bacteria were cultured in media for 3 to 4 hours, and thereafter absorbances at $A_{600}$ were measured. Bacterial suspensions were diluted with Mueller-Hinton broth (MHB) according to McFarland #0.5. Each strain was added so as to attain about $0.5-1\times10^5$ CFU/mL (final concentration) in terms of *Escherichia coli*. Each peptide was prepared and added to a microplate or test tubes so as to attain a final concentration of 1.0 μg/mL, and the bacterial suspension was added thereto. A solution to which the peptides were not added was considered as a negative and a solution to which tobramycin (TOB) (1 μg/mL) was added was considered as a positive control. The plate was incubated at 37° C. for 3 hours, and the amount of ATP in the culture media was measured. Relative values were calculated by comparison with the negative control, and these values were regarded as the viability.

The results are shown in Table 2. In the table, "ND" means there are no data.

TABLE 2

| | Viability (%) | |
|---|---|---|
| Compound | *P. aeruginosa* | *S. aureus* |
| TOB (tobramycin) | 1.8 | 3.6 |
| SRP-7 | 1.5 | 5.5 |
| SRP-8 | 1.7 | 3.6 |
| SRP-9 | 1.8 | 1.9 |
| SRP-10 | 6.5 | 6.0 |
| SRP-11 | 1.3 | 2.6 |
| SRP-12 | 1.7 | 0.4 |
| SRP-13 | 1.6 | 7.1 |
| SRP-14 | 1.5 | 0.6 |
| SRP-15 | 1.6 | 6.1 |
| SRP-16 | 1.3 | 3.9 |
| SRP-17 | 1.4 | 6.6 |
| Ovispirin-1 | ND | 3.2 |

As shown in Table 2, each of the polypeptides of the present invention exhibited antibacterial activity against *Pseudomonas aeruginosa* or *Staphylococcus aureus* comparable to TOB. The polypeptides of the present invention exhibited antibacterial activity against *Staphylococcus aureus* about the same as Ovispirin-1.

4. Measurement of Antibacterial and Antifungal Activities

Further, the peptides shown in Table 3 below were synthesized by the same method as described above, and the antibacterial activity (including antifungal activity) and/or ATP activity thereof were examined together with the above-described peptides.

TABLE 3

| No. | N-terminal | Amino acid sequence | C-terminal | SEQ ID NO |
|---|---|---|---|---|
| SRP-18 | Ac | GRLKRMGKRLKRKIQKWARW | amide | SEQ ID NO: 13 |
| SRP-19 | Ac | GRLKRMGERLKRKIQKWIRW | amide | SEQ ID NO: 14 |
| SRP-20 | Ac | KLIFLRELRRLKRKLKRKLR | amide | SEQ ID NO: 15 |
| SRP-21 | | GRLKRMGERLKRKIQKLIRL | amide | SEQ ID NO: 16 |
| SRP-22 | | GRLKRLGERLKRKIQKWIRW | amide | SEQ ID NO: 17 |
| SRP-23 | | GRLKRVGERLKRKIQKWIRW | amide | SEQ ID NO: 18 |

TABLE 3-continued

| No. | N-terminal | Amino acid sequence | C-terminal | SEQ ID NO |
|---|---|---|---|---|
| SRP-24 | | GRLKRIGERLKRKIQKWIRW | amide | SEQ ID NO: 19 |
| SRP-25 | | MGERLKRKIQKWIRW | amide | SEQ ID NO: 20 |
| SRP-26 | | GERLKRKIQKWIRW | amide | SEQ ID NO: 21 |
| SRP-27 | | GRLKRLGERLKRKIQKLIRL | amide | SEQ ID NO: 22 |
| SRP-28 | | RLKRLGERLKRKIQKLIRL | amide | SEQ ID NO: 23 |
| SRP-29 | | LKRLGERLKRKIQKLIRL | amide | SEQ ID NO: 24 |
| SRP-30 | | KRLGERLKRKIQKLIRL | amide | SEQ ID NO: 25 |
| SRP-31 | | RLGERLKRKIQKLIRL | amide | SEQ ID NO: 26 |
| SRP-32 | | GRLKRLGKRLKRKIQKLARL | amide | SEQ ID NO: 27 |
| SRP-33 | Ac | RLKRLGERLKRKIQKLIRL | amide | SEQ ID NO: 28 |
| SRP-34 | | RLKRLGERLKRKIQKLIR | amide | SEQ ID NO: 29 |
| SRP-35 | | RLKRLGERLKRKIQKLI | amide | SEQ ID NO: 30 |
| SRP-36 | | RLKRLGERLKRKIQKL | amide | SEQ ID NO: 31 |

("Ac" means acetylation and "Amide" means amidation)

Mold fungi (*Aspergillus niger* NBRC 9455, *Rhizopus oryzae* NBRC 31005, *Fusarium solani* JCM11383, *Alternaria alternata* JCM5800, *Trichophyton mentagrophytes* NBRC6124 and *Trichophyton rubrum* NBRC9185) were inoculated to potato-dextrose agar medium and cultured at 35° C. (or at a temperature appropriate for the generation of conidium (spore) of each strain) until the conidium was formed (for about 7 days). The conidia (spores) were collected and suspended in 0.1% Tween 80-containing physiological saline. By filtration through a sterilized cotton filter and centrifugation, the components originated from the medium and the mycelia were removed.

The absorbance at 530 nm of the conidium (spore) suspension was measured, and the number of the conidia (spores) in the suspension was measured by the plate dilution method. From the relationship between the absorbance and the number of the conidia (spores), a calibration, curve of the conidia (spores) was obtained to determine the number of the conidia (spores) to be inoculated in the measurement of the antifungal activity.

Yeast fungi (*Cryptococcus neoformans* IFM 46660 and *Candida krusei* NBRC1395) were inoculated to Sabouraud-dextrose agar medium and cultured at 35° C. for 2 days. From the formed colonies, the strains were subcultured to a fresh agar medium and cultured at 35° C. for 2 days. This step was repeated one more time and each strain was isolated, which was used as the fungal cells for the tests. The obtained fungal cells were collected and suspended in sterilized physiological saline to obtain a fungal cell suspension. The absorbance at 530 nm of this suspension was measured and the number of the fungal cells in the suspension was measured by the plate dilution method. From the relationship between the absorbance and the number of the fungal cells, a calibration curve of the fungal cells was obtained to determine the number of the fungal cells to be inoculated in the measurement of the antifungal activity.

Each of the bacteria (*Micrococcus luteus* NBRC13867, *Bacillus subtilis* NBRC3134, *Salmonella enteritidis* IID 604, *Salmonella typhimurium* JCM1652, *Streptococcus pyogenes* JCM5674, *Acinetobacter baumanni* JCM6841, *Bacteroides fragilis* JCM 11019, *Fusobacterium nucleatum* JCM 11025 and *Actinobacillus actinomycetemcomitans* JCM2434) was inoculated to SCD or GAM agar medium, and cultured at a temperature and period suited for the strain (cultured anaerobically as required). From the thus obtained colonies, each strain was inoculated to a fresh agar medium and cultured. This step was repeated one more time to isolate a strain, which was used as the bacterial cells for the test. The absorbance at 530 nm of the suspension in which the thus obtained bacterial cells were suspended was measured and the number of the bacterial cells in the suspension was measured by the plate dilution method. From the relationship between the absorbance and the number of the bacterial cells, a calibration curve of the bacterial cells was obtained to determine the number of the bacterial cells to be inoculated in the measurement of the antibacterial activity.

Each of the thus prepared suspensions of the cells or conidia was diluted with physiological saline to $2\times10^5$ to $2.5\times10^6$ CFU/mL using the above-described calibration curve of the number of the cells or conidia, and further 50-fold diluted with the medium to prepare an inoculation solution of $0.4\times10^4$ to $5\times10^4$ CFU/mL.

The peptide solution to be tested was diluted with sterilized purified water to prepare a solution of 12.80 μg/mL. This solution was serially diluted with sterilized purified water, and further 5-fold diluted with the medium to prepare peptide containing media having concentrations of 256, 128, 64, 32, 16, 8.0, 4.0, 2.0, 1.0, 0.5, 0.25 and 0.125 μm/mL, respectively. As a positive control, amphotericin B was used for mold fungi and yeast fungi, and chloramphenicol was used for bacteria. Each of amphotericin. B and chloramphenicol was dissolved in DMSO to a concentration of 12,800 μg/mL and then serially diluted with DMSO, followed by 50-fold dilution with the medium to prepare amphotericin B- or chloramphenicol-containing media having concentrations of 256, 128, 64, 32, 16, 8.0, 4.0, 2.0, 1.0, 0.5, 0.25 and 0.125 μg/mL, respectively.

To a 96-well microtiter plate, 0.1 mL of the inoculation solution and 0.1 mL of the peptide- or positive control-containing medium having the respective concentration were added, and each strain was cultured at a temperature suited for the respective strain for 16 to 50 hours (or a time suited for the growth of the respective strain). The concentrations when the peptide, amphotericin B or chloramphenicol was subjected to the measurement were 128, 64, 32, 16, 8, 4, 2, 1.0, 0.5, 0.25, 0.12 and 0.0625 µg/mL, respectively. The well not containing the sample was used as a negative control. After the culturing for a time period appropriate for the respective strain, the growth was visually observed, and the minimum concentration at which the growth was inhibited was defined as the minimum growth inhibition concentration (MIC).

The medium used was RPMI-1640 (containing glutamic acid, not containing carbonate and containing Phenol Red) in the tests for mold fungi and yeast fungi, and was Muller-Hinton broth or *Brucella* broth in the tests for bacteria. Independent experiments were carried out twice for each strain.

Bacteria (*Escherichia coli* ATCC 25922, *Pseudomonas aeruginosa* ATCC 27853, *Staphylococcus aureus* ATCC29213, *Klebsiella pneumoniae* JCM 1662, *Enterobacter cloacae* JCM 1232, *Enterobacter aerogenes* JCM 1235 and *Staphylococcus epidermidis* JCM 2414) were inoculated to Mueller-Hinton broth: MHB or LB medium, and cultured at a temperature and period suited for each strain. From the thus obtained colonies, each strain was inoculated to a fresh liquid medium and cultured for 16 to 20 hours. Then an aliquot having a volume (10 to 50 appropriate to each strain was inoculated to a fresh liquid medium and cultured for 4 to 6 hours, followed by the measurement of the absorbance at 600 nm. After comparing the turbidity with McFarland #0.5, the resultant was diluted with a medium. Each strain was added to about $10^5$ CFU/mL (final concentration).

Further, the antibacterial activities against the clinical strains collected and isolated from infected patients were also examined. The tests were carried out for two methicillin-resistant *Staphylococcus* (MRSA) (MRSA (i) and (ii)), two methicillin-sensitive *Staphylococcus* (MSSA) (MSSA (i) and (ii)), five *Pseudomonas aeruginosa*, Pseudomonas aeruginosa 1, Pseudomonas aeruginosa 6, *Pseudomonas aeruginosa* 8. *Pseudomonas aeruginosa* 9 and *Pseudomonas aeruginosa* 12, totally 9 clinical strains. The MRSA and MSSA clinical strains were tested by the same method as *Staphylococcus aureus* ATCC29213, and *Pseudomonas* clinical strains were tested by the same method as *Pseudomonas aeruginosa* ATCC 27853.

Each of the peptide solutions to be tested was diluted with MHB to obtain a solution of 128 µg/mL. This solution was serially diluted with the medium to prepare peptide-containing media having concentrations of 128, 64, 32, 16, 8.0, 4.0 and 2.0 µg/mL respectively. As controls, tobramycin (TOB: aminoglucoside antibiotic), oxacillin (OX:β-lactam antibiotic), meropenem (MEPM: carbapenem antibiotic) and ciprofloxacin (new quinolone antibiotic) were used. By dilution with sterilized purified water to 1.0 mg/mL, positive control-containing media having concentrations of 16, 8, 4, 2, 1.0, 0.25, 0.12 and 0.06 µg/mL, respectively for TOB; 0.5, 0.12 and 0.06 µg/mL, respectively, for OX; and 16, 8, 4, 2, 1.0, 0.25, 0.12, 0.06, 0.06, 0.03 and 0.008 µg/mL, respectively, for MEPM, were prepared.

To a 96-well microtiter plate, 0.1 mL of the inoculation solution and 0.1 mL of the peptide- or positive control-containing medium having the respective concentration were added, and cultured at 37° C. for 16 to 24 hours (or a time period suited for the growth of the respective strain). The well not containing the sample was used as a negative control. After the culturing, the growth was visually observed, and the minimum concentration at which the growth was inhibited was defined as the minimum growth inhibition concentration (MIC).

The medium used in this test for bacteria was Mueller-Hinton broth. Independent experiments were carried out twice or more for each strain.

The results are shown in Table 4 and Table 5.

Antibacterial activity of each sample against each strain (MIC)

Table 4-1

| | | SRP-15 | SRP-14 | SRP-16 | SRP-8 | SRP-13 | SRP-12 | SRP-9 | SRP-11 |
|---|---|---|---|---|---|---|---|---|---|
| Aerobic bacteria | *Micrococcus luteus* | 4 | 4 | 2 | 2 | 2 | N.T. | N.T. | N.T. |
| | *Bacillus subtilis* | 4 | 4 | 8/4 | 8 | 4 | N.T. | N.T. | N.T. |
| | *Salmonella Enteritidis* | 8/16 | 4 | 4 | 64 | 4 | N.T. | N.T. | N.T. |
| | *Salmonella Typhimurium* | 8/4 | 4/8 | 8 | 64 | 4 | N.T. | N.T. | N.T. |
| | *Streptococcus pyogenes* | 16 | 16 | 32 | 64 | 32 | N.T. | N.T. | N.T. |
| Anaerobic bacteria | *Acinetobacter baumanni* | 32 | 64 | 128 | 128 | 16/32 | N.T. | N.T. | N.T. |
| | *Bacteroides fragilis* | 16 | 128 | 32 | >128 | 64 | N.T. | N.T. | N.T. |
| | *Fusobacterium nucleatum* | 4 | 4 | 128 | >128 | 4 | N.T. | N.T. | N.T. |
| | *Actinobacillus actinomycetemcomitans* | 32 | 64 | 128 | >128 | 128 | N.T. | N.T. | N.T. |
| Fungi | *Fusarium solani* | 16/32 | 4 | 4/8 | 4 | 4/8 | N.T. | N.T. | N.T. |
| | *Alternaria alternata* | 64 | 32 | 64 | 32 | 64 | N.T. | N.T. | N.T. |
| | *Trichophyton mentagrophytes* | 32 | 16 | 32 | 32 | 32 | N.T. | N.T. | N.T. |
| | *Trichophyton rubrum* | 64 | 32 | 64/32 | 128 | 128/64 | N.T. | N.T. | N.T. |
| | *Candida krusei* | 16 | 32 | 32 | 32 | 32 | N.T. | N.T. | N.T. |
| | *Aspergillus niger* | 8/16 | 4/8 | 8/16 | 16/32 | 16 | 8/16 | 16/32 | 8/32 |
| | *Cryptococcus neoformans* | 2 | 1 | 2 | 1/2 | 2 | 1 | 1/2 | 2 |
| | *Rhizopus oryzae* | 16 | 8 | 8/16 | 8 | 8 | 8 | 8 | 8 |
| Bacteria | *Escherichia coli* | 16 | 16 | 16/32 | 16/32 | 16/32 | 32 | 32 | 32/64 |
| | *Pseudomonas aeruginosa* | 16 | 16 | 16 | 16 | 16 | 16/32 | 16 | 16 |
| | *Staphylococcus aureus* | 16 | 16 | 16 | 16 | 32 | 16 | 16/32 | 16 |
| | *Klebsiella pneumoniae* | 16 | 16/128 | 64 | 32 | 32 | 128 | 64 | 64/128 |
| | *Enterobacter cloacae* | 16/32 | 32/128 | 64 | 128< | 32/64 | 128< | 16/64 | 128< |
| | *Enterobacter aerogenes* | 16 | 16/32 | 16/32 | 64 | 16/64 | 32/64 | 16/64 | 32/64 |
| | *Staphylococcus epidermidis* | 8 | 8/16 | 8/16 | 8/16 | 4/8 | 4/8 | 8/32 | 8 |

-continued

Antibacterial activity of each sample against each strain (MIC)

| | | | | | | | | | |
|---|---|---|---|---|---|---|---|---|---|
| Clinical strains | Pseudomonas aeruginosa 1 | 16 | 16 | 16/32 | 16/32 | 16/32 | 16/32 | 16/32 | 16/32 |
| | Pseudomonas aeruginosa 6 | 16 | 8/16 | 16 | 16 | 8/16 | 32/64 | 16/64 | 16/32 |
| | Pseudomonas aeruginosa 8 | 16 | 16 | 16 | 16 | 16 | 32/64 | 8/32 | 16/32 |
| | Pseudomonas aeruginosa 9 | 8/64 | 16/32 | 64 | 16/64 | 64 | 16/64 | 32/128 | 16/32 |
| | Pseudomonas aeruginosa 12 | 8/16 | 8/16 | 8/16 | 16/32 | 8/16 | 16 | 16/32 | 16 |
| | MSSA(i) | 16/32 | 16/32 | 16/32 | 32/64 | 16/32 | 16 | N.T. | N.T. |
| | MSSA(ii) | 16 | 16/32 | 16 | 32 | 16 | 16 | N.T. | N.T. |
| | MRSA(i) | 16 | 16/32 | 32 | 64 | 64 | 32 | N.T. | N.T. |
| | MRSA(ii) | 16/32 | 16/32 | 64 | 64 | 64 | 32/64 | N.T. | N.T. |

Table 4-2

| | | SRP-7 | SRP-17 | SRP-10 | SRP-18 | SRP-19 | SRP-20 | SRP-21 | Ovispirin-1 |
|---|---|---|---|---|---|---|---|---|---|
| Aerobic bacteria | Micrococcus luteus | 2 | 1 | N.T. | 1 | 2 | 2 | 1 | 2 |
| | Bacillus subtilis | 4 | 8 | N.T. | 2 | 2 | 2 | 2 | 2 |
| | Salmonella Enteritidis | 4 | 8 | N.T. | 2 | 4 | 4 | 2 | 16 |
| | Salmonella Typhimurium | 4 | 16 | N.T. | 4/2 | 4 | 4 | 2 | 16 |
| | Streptococcus pyogenes | 32 | 128 | N.T. | 16 | 16 | 32 | 8 | 32 |
| Anaerobic bacteria | Acinetobacter baumanni | 128 | 128 | N.T. | 32 | 32 | 16 | 32 | 4/8 |
| | Bacteroides fragilis | 128 | >128 | N.T. | 64/32 | 16/8 | 8/16 | 16 | 1 |
| | Fusobacterium nucleatum | 4 | >128 | N.T. | 32/16 | 4 | 4 | 4 | 2/4 |
| | Actinobacillus actinomycetemcomitans | 128 | >128 | N.T. | 64 | 64 | 128 | 32 | 128 |
| Fungi | Fusarium solani | 8 | 8 | N.T. | 8 | 16 | 4 | 16 | 4/8 |
| | Alternaria alternata | 32 | 32 | N.T. | 32 | 64 | 32/64 | 64 | 64 |
| | Trichophyton mentagrophytes | 32 | 16 | N.T. | 16 | 32 | 16 | 64 | 32 |
| | Trichophyton rubrum | 64/32 | 64/32 | N.T. | 32 | 64 | 32 | 128 | 64 |
| | Candida krusei | 64/32 | 32 | N.T. | 32/16 | 16 | 16 | 32 | 16 |
| | Aspergillus niger | 8/16 | 8/16 | 8/16 | N.T. | N.T. | N.T. | N.T. | 32 |
| | Cryptococcus neoformans | 2 | 2 | 2 | N.T. | N.T. | N.T. | N.T. | 2/4 |
| | Rhizopus oryzae | 8/16 | 8 | 8 | N.T. | N.T. | N.T. | N.T. | >128 |
| Bacteria | Escherichia coli | 32 | 16/32 | 32/64 | 8/16 | 8/16 | 8/16 | 16/32 | 8/16 |
| | Pseudomonas aeruginosa | 8/16 | 32/64 | 16/32 | 4/8 | 8 | 8/16 | 8 | 16/32 |
| | Staphylococcus aureus | 32 | 16/32 | 16 | 8/16 | 8 | 16 | 8/32 | 16 |
| | Klebsiella pneumoniae | 16/64 | 32 | 64/128 | N.T. | N.T. | N.T. | N.T. | 8/16 |
| | Enterobacter cloacae | 16/128 | 128< | 64/128 | N.T. | N.T. | N.T. | N.T. | 32/64 |
| | Enterobacter aerogenes | 16/64 | 128 | 16/128 | N.T. | N.T. | N.T. | N.T. | 16/32 |
| | Staphylococcus epidermidis | 8 | 4/8 | 8 | 8 | 8 | 8-16 | 8-16 | 8/16 |
| Clinical strains | Pseudomonas aeruginosa 1 | 32/64 | 32/64 | 16/64 | N.T. | N.T. | N.T. | N.T. | 16/64 |
| | Pseudomonas aeruginosa 6 | 16/64 | 32/64 | 32/128 | N.T. | N.T. | N.T. | N.T. | 32/64 |
| | Pseudomonas aeruginosa 8 | 32 | 64/128 | 64/128 | N.T. | N.T. | N.T. | N.T. | 32/64 |
| | Pseudomonas aeruginosa 9 | 64/128 | 64/128 | 64/128 | N.T. | N.T. | N.T. | N.T. | 32/128 |
| | Pseudomonas aeruginosa 12 | 16 | 16/64 | 16/32 | N.T. | N.T. | N.T. | N.T. | 16/32 |
| | MSSA(i) | N.T. | N.T. | N.T. | N.T. | N.T. | N.T. | N.T. | 16/32 |
| | MSSA(ii) | N.T. | N.T. | N.T. | N.T. | N.T. | N.T. | N.T. | 16 |
| | MRSA(i) | N.T. | N.T. | N.T. | N.T. | N.T. | N.T. | N.T. | 32 |
| | MRSA(ii) | N.T. | N.T. | N.T. | N.T. | N.T. | N.T. | N.T. | 32 |

Table 4-3

| | | chloramphenicol | amphotericin B | tobramycin | meropenem | oxacillin | ciprofloxacin |
|---|---|---|---|---|---|---|---|
| Aerobic bacteria | Micrococcus luteus | 1 | N.T. | N.T. | N.T. | N.T. | N.T. |
| | Bacillus subtilis | 4 | N.T. | N.T. | N.T. | N.T. | N.T. |
| | Salmonella Enteritidis | 4 | N.T. | N.T. | N.T. | N.T. | N.T. |
| | Salmonella Typhimurium | 4 | N.T. | N.T. | N.T. | N.T. | N.T. |
| | Streptococcus pyogenes | 2 | N.T. | N.T. | N.T. | N.T. | N.T. |
| Anaerobic bacteria | Acinetobacter baumanni | 16/32 | N.T. | N.T. | N.T. | N.T. | N.T. |
| | Bacteroides fragilis | 1 | N.T. | N.T. | N.T. | N.T. | N.T. |
| | Fusobacterium nucleatum | 0.25 | N.T. | N.T. | N.T. | N.T. | N.T. |
| | Actinobacillus actinomycetemcomitans | 0.5 | N.T. | N.T. | N.T. | N.T. | N.T. |
| Fungi | Fusarium solani | N.T. | 1 | N.T. | N.T. | N.T. | N.T. |
| | Alternaria alternata | N.T. | 1 | N.T. | N.T. | N.T. | N.T. |
| | Trichophyton mentagrophytes | N.T. | 0.125 | N.T. | N.T. | N.T. | N.T. |
| | Trichophyton rubrum | N.T. | 0.25 | N.T. | N.T. | N.T. | N.T. |
| | Candida krusei | N.T. | 2 | N.T. | N.T. | N.T. | N.T. |
| | Aspergillus niger | N.T. | 0.25/0.5 | N.T. | N.T. | N.T. | N.T. |
| | Cryptococcus neoformans | N.T. | 0.25/0.5 | N.T. | N.T. | N.T. | N.T. |
| | Rhizopus oryzae | N.T. | 0.125/0.25 | N.T. | N.T. | N.T. | N.T. |
| Bacteria | Escherichia coli | N.T. | N.T. | 0.25-1.0 | 0.008-0.06 | N.T. | N.T. |
| | Pseudomonas aeruginosa | N.T. | N.T. | 0.25-1.0 | 0.25-1.0 | N.T. | N.T. |
| | Staphylococcus aureus | N.T. | N.T. | 0.12-1.0 | 0.03-0.12 | 0.15-0.5 | N.T. |
| | Klebsiella pneumoniae | N.T. | N.T. | 4> | 4> | N.T. | N.T. |
| | Enterobacter cloacae | N.T. | N.T. | 4> | 4> | N.T. | N.T. |
| | Enterobacter aerogenes | N.T. | N.T. | 4> | 4> | N.T. | N.T. |
| | Staphylococcus epidermidis | N.T. | N.T. | 0.12-1.0 | 0.03-0.12 | 0.15-0.5 | N.T. |

-continued

Antibacterial activity of each sample against each strain (MIC)

| | | | | | | | |
|---|---|---|---|---|---|---|---|
| Clinical strains | *Pseudomonas aeruginosa* 1 | N.T. | N.T. | 16< | 4> | N.T. | 2> |
| | *Pseudomonas aeruginosa* 6 | N.T. | N.T. | 4> | 8-16 | N.T. | 2> |
| | *Pseudomonas aeruginosa* 8 | N.T. | N.T. | 4> | 4> | N.T. | 2> |
| | *Pseudomonas aeruginosa* 9 | N.T. | N.T. | 4> | 4> | N.T. | 2> |
| | *Pseudomonas aeruginosa* 12 | N.T. | N.T. | 4> | 4> | N.T. | 4< |
| | MSSA(i) | N.T. | N.T. | 4> | 4> | 8 | N.T. |
| | MSSA(ii) | N.T. | N.T. | 4 | 4-8 | 2 | N.T. |
| | MRSA(i) | N.T. | N.T. | 16< | 4> | 4> | N.T. |
| | MRSA(ii) | N.T. | N.T. | 16< | 8-16 | 8< | N.T. | unit: concentration (mg/mL) (same in Table 4-2 and Table 4-3)
*In cases where the MICs measured in the two tests were identical, the number of the values in each cell is one, and in cases where they were not identical, each of the values measured in the first/second tests are shown (same in Table 4-2 and Table 4-3).
*N.T.: not tested (same in Table 4-2 and Table 4-3).

Table 5-1

| | SRP-22 | SRP-23 | SRP-24 | SRP-25 | SRP-26 | SRP-27 | SRP-28 | SRP-29 |
|---|---|---|---|---|---|---|---|---|
| *Escherichia coli* | 8-16 | 16 | 16 | 16 | 16-32 | 16 | 16 | 16-32 |
| *Pseudomonas aeruginosa* | 8-16 | 8-16 | 8-16 | 16 | 16 | 8-16 | 4-8 | 8 |
| *Staphylococcus aureus* | 8-16 | 8-16 | 16 | 16 | 16 | 16 | 16 | 16-32 |
| *Staphylococcus epidermidis* | 8 | 8-16 | 8-32 | 8-32 | 16-32 | 8-16 | 8-16 | 8 |

Table 5-2

| | SRP-30 | SRP-31 | SRP-32 | SRP-33 | SRP-34 | SRP-35 | SRP-36 |
|---|---|---|---|---|---|---|---|
| *Escherichia coli* | 64 | 32-64 | 16 | 8-16 | 8-16 | 8-16 | 16-32 |
| *Pseudomonas aeruginosa* | 8-16 | 16 | 8-16 | 8-16 | 8-16 | 8-16 | 8-16 |
| *Staphylococcus aureus* | 16-64 | 32-64 | 16 | 16 | 16-32 | 16-32 | 16-32 |
| *Staphylococcus epidermidis* | 8-16 | 8-16 | 4-8 | 8-16 | 8-16 | 8 | 8 |

As shown in Tables 4 and 5, each of the peptides exhibited antibacterial activity.

5. ATP Assay

Bacteria (*Escherichia coli* ATCC 25922, *Pseudomonas aeruginosa* ATCC 27853, *Staphylococcus aureus* ATCC29213, and *Staphylococcus epidermidis* JCM 2414) were inoculated to Mueller-Hinton broth: MHB or LB medium, and cultured at a temperature and period suited for each strain. From the thus obtained colonies, each strain was inoculated to a fresh liquid medium and cultured for 16 to 20 hours. Then an aliquot having a volume (10 to 50 μL) appropriate to each strain was inoculated to a fresh liquid medium and cultured for 4 to 6 hours, followed by the measurement of the absorbance at 600 nm. After comparing the turbidity with McFarland #0.5, the resultant was diluted with a medium. Each strain was added to about $10^5$ CFU/mL (final concentration).

Each of the peptide solutions to be tested was diluted with the medium to obtain a solution of 10 μg/mL. As positive controls, tobramycin (TOB), oxacillin (OX) and meropenem (MEPM) were used. By dilution with sterilized purified water to 1.0 mg/mL, positive control-containing media having concentrations of 1.0, 0.25, 0.12 and 0.06 mg/mL, respectively for TOB; 0.5, 0.12 and 0.06 μg/mL, respectively, for OX; and 1.0, 0.25, 0.12, 0.06, 0.03 and 0.008 μg/mL respectively, for MEPM, were prepared. To a 96-well microtiter plate, 0.1 mL of the inoculation solution and 0.1 mL of the peptide- or positive control-containing medium having the respective concentration were added, and cultured at 37° C. for 3 hours. The well not containing the sample was used as a negative control. After the culturing, ATP was measured using BacTiter-Glo Microbial Cell Viability Assay kit of PROMEGA, and compared with that in the negative control to obtain a relative value which was defined as a viability. The antibacterial activity was evaluated based on the viability at 3 hours later using ATP as an index.

The medium used in this test for bacteria was Mueller-Hinton broth. Independent experiments were carried out twice for each strain.

The results are shown in Table 6 below.

TABLE 6

| | *Escherichia coli* ATP | *Pseudomonas aeruginosa* ATP | *Staphylococcus aureus* ATP |
|---|---|---|---|
| SRP-15 | 0.5 | 1.6 | 0.3 |
| SRP-14 | 1.2 | 1.0 | 0.3 |
| SRP-16 | 0.9 | 1.0 | 0.4 |
| SRP-8 | 1.7 | 0.9 | 0.4 |
| SR-13 | 2.2 | 2.2 | 2.0 |
| SRP-12 | 6.5 | 1.0 | 0.2 |
| SRP-9 | 2.6 | 0.8 | 0.2 |
| SRP-11 | 3.8 | 0.8 | 0.3 |
| SRP-7 | 1.6 | 1.0 | 0.2 |
| SRP-17 | 0.4 | 1.0 | 0.3 |
| SRP-10 | 2.4 | 0.9 | 0.2 |
| SRP-18 | 1.7 | 1.5 | 2.0 |
| SRP-19 | 2.9 | 1.6 | 2.1 |
| SRP-20 | 6.2 | 1.1 | 3.2 |
| SRP-22 | 4.5 | 1.4 | 5.0 |
| SRP-23 | 2.8 | 1.5 | 3.0 |
| SRP-24 | 8.2 | 1.3 | 2.7 |
| SRP-25 | 23.5 | 15.4 | 10.9 |
| SRP-26 | 9.0 | 6.2 | 12.9 |
| SRP-21 | 3.7 | 3.8 | 1.8 |
| SRP-27 | 5.6 | 2.1 | 3.2 |
| SRP-28 | 7.1 | 1.4 | 5.2 |
| SRP-29 | 9.0 | 1.8 | 1.9 |
| SRP-30 | 19.9 | 2.0 | 6.3 |
| SRP-31 | 27.4 | 9.7 | 19.7 |
| SRP-32 | 7.0 | 1.6 | 5.2 |
| SRP-33 | 2.9 | 2.8 | 1.6 |
| SRP-34 | 4.4 | 2.8 | 2.6 |
| SRP-35 | 3.6 | 5.2 | 2.1 |
| SRP-36 | 6.4 | 2.0 | 3.6 |
| tobramycin | 74.3 | 1.2 | 6.7 |
| oxacillin | 142.0 | 100.3 | 121.2 |
| meropenem | 15.3 | 16.1 | 15.7 |

From Table 6, it was shown that these peptides exhibited antibacterial activity in terms of ATP activity against any of the three strains tested, so that it was suggested that any of these peptides have a wide antibacterial spectrum.

The invention claimed is:

1. A polypeptide comprising the amino acid of SEQ ID NO:9.

2. The polypeptide of claim 1, wherein the carboxyl-terminal of said polypeptide is amidated.

3. The polypeptide of claim 1, wherein the amino-terminal of said polypeptide is acetylated.

4. The polypeptide of claim 2, wherein the amino-terminal of said polypeptide is acetylated.

5. The polypeptide of claim 1, wherein said polypeptide consists of the amino acid of SEQ ID NO:9.

6. The polypeptide of claim 5, wherein the carboxyl-terminal of said polypeptide is amidated.

7. The polypeptide of claim 5, wherein the amino-terminal of said polypeptide is acetylated.

8. The polypeptide of claim 6, wherein the amino-terminal of said polypeptide is acetylated.

9. An antibacterial, an antifungal and/or an antiseptic composition comprising as an effective ingredient the polypeptide of claim 1.

10. The antibacterial, the antifungal and/or the antiseptic composition of claim 9, wherein the carboxyl-terminal of said polypeptide is amidated.

11. The antibacterial, the antifungal and/or the antiseptic composition of claim 9, wherein the amino-terminal of said polypeptide is acetylated.

12. The antibacterial, the antifungal and/or the antiseptic composition of claim 10, wherein the amino-terminal of said polypeptide is acetylated.

13. The antibacterial, the antifungal and/or the antiseptic composition of claim 9, further comprising a base material coated with impregnated with said polypeptide.

14. The antibacterial, the antifungal and/or the antiseptic composition of claim 13, wherein said base material is a gauze, bandage, cotton, woven fabric, non-woven fabric, knit, knitted fabric, compression sheet, or compression fabric or paper.

15. The antibacterial, the antifungal and/or the antiseptic composition of claim 9 wherein said composition is in the form of a spray.

16. A method for disinfection using an antibacterial, an antifungal or an antiseptic agent, said method comprising administering or applying an effective amount of the polypeptide of claim 1.

17. The method of claim 16, wherein said polypeptide is applied to a medical instrument or to fingers for disinfection.

18. The method of claim 16, wherein said polypeptide is applied or administered as a spray.

19. The method of claim 16, wherein the carboxyl-terminal of said polypeptide is amidated the amino-terminal of said polypeptide is acetylated.

* * * * *

SEQUENCE LISTING

<160> NUMBER OF SEQ ID NOS: 31

<210> SEQ ID NO 1
<211> LENGTH: 20
<212> TYPE: PRT
<213> ORGANISM: Artificial Sequence
<220> FEATURE:
<223> OTHER INFORMATION: SRP-7, chemically synthesized peptide

<400> SEQUENCE: 1

Ile Phe Leu His Arg Leu Lys Arg Met Arg Lys Arg Leu Lys Arg Lys
1               5                   10                  15

Leu Arg Leu Trp
            20

<210> SEQ ID NO 2
<211> LENGTH: 22
<212> TYPE: PRT
<213> ORGANISM: Artificial Sequence
<220> FEATURE:
<223> OTHER INFORMATION: SRP-8, chemically synthesized peptide

<400> SEQUENCE: 2

Arg Leu Lys Arg Met Arg Lys Arg Leu Lys Arg Lys Leu Arg Leu Trp
1               5                   10                  15

His Arg Lys Arg Tyr Lys
            20

<210> SEQ ID NO 3
<211> LENGTH: 22
<212> TYPE: PRT
<213> ORGANISM: Artificial Sequence
<220> FEATURE:
<223> OTHER INFORMATION: SRP-9, chemically synthesized peptide

<400> SEQUENCE: 3

Met Leu Lys Leu Ile Phe Leu His Arg Leu Lys Arg Met Arg Lys Arg
1               5                   10                  15

Leu Lys Arg Lys Leu Arg
            20

<210> SEQ ID NO 4
<211> LENGTH: 20
<212> TYPE: PRT
<213> ORGANISM: Artificial Sequence
<220> FEATURE:
<223> OTHER INFORMATION: SRP-10, chemically synthesized peptide

<400> SEQUENCE: 4

Met Leu Lys Leu Ile Phe Leu His Arg Leu Lys Arg Met Arg Lys Arg
1               5                   10                  15

Leu Lys Arg Lys
            20

<210> SEQ ID NO 5
<211> LENGTH: 20
<212> TYPE: PRT
<213> ORGANISM: Artificial Sequence
<220> FEATURE:
<223> OTHER INFORMATION: SRP-11, chemically synthesized peptide

<400> SEQUENCE: 5

Leu Lys Leu Ile Phe Leu His Arg Leu Lys Arg Met Arg Lys Arg Leu
1               5                   10                  15

```
Lys Arg Lys Leu
        20

<210> SEQ ID NO 6
<211> LENGTH: 20
<212> TYPE: PRT
<213> ORGANISM: Artificial Sequence
<220> FEATURE:
<223> OTHER INFORMATION: SRP-12, chemically synthesized peptide

<400> SEQUENCE: 6

Leu Ile Phe Leu His Arg Leu Lys Arg Met Arg Lys Arg Leu Lys Arg
1               5                   10                  15

Lys Leu Arg Leu
        20

<210> SEQ ID NO 7
<211> LENGTH: 21
<212> TYPE: PRT
<213> ORGANISM: Artificial Sequence
<220> FEATURE:
<223> OTHER INFORMATION: SRP-13, chemically synthesized peptide

<400> SEQUENCE: 7

Lys Leu Ile Phe Leu His Arg Leu Lys Arg Glu Leu Arg Lys Arg Leu
1               5                   10                  15

Lys Arg Lys Leu Arg
        20

<210> SEQ ID NO 8
<211> LENGTH: 20
<212> TYPE: PRT
<213> ORGANISM: Artificial Sequence
<220> FEATURE:
<223> OTHER INFORMATION: SRP-14, chemically synthesized peptide

<400> SEQUENCE: 8

Gly Arg Leu Lys Arg Met Gly Lys Arg Leu Lys Arg Lys Ile Gln Lys
1               5                   10                  15

Trp Ala Arg Trp
        20

<210> SEQ ID NO 9
<211> LENGTH: 20
<212> TYPE: PRT
<213> ORGANISM: Artificial Sequence
<220> FEATURE:
<223> OTHER INFORMATION: SRP-15, chemically synthesized peptide

<400> SEQUENCE: 9

Gly Arg Leu Lys Arg Met Gly Glu Arg Leu Lys Arg Lys Ile Gln Lys
1               5                   10                  15

Trp Ile Arg Trp
        20

<210> SEQ ID NO 10
<211> LENGTH: 20
<212> TYPE: PRT
<213> ORGANISM: Artificial Sequence
<220> FEATURE:
<223> OTHER INFORMATION: SRP-16, chemically synthesized peptide

<400> SEQUENCE: 10

Lys Leu Ile Phe Leu Arg Glu Leu Arg Arg Leu Arg Lys Arg Leu Lys
1               5                   10                  15
```

```
Arg Lys Leu Arg
            20

<210> SEQ ID NO 11
<211> LENGTH: 16
<212> TYPE: PRT
<213> ORGANISM: Artificial Sequence
<220> FEATURE:
<223> OTHER INFORMATION: SRP-17, chemically synthesized peptide

<400> SEQUENCE: 11

Arg Leu Lys Arg Met Arg Lys Arg Leu Lys Arg Lys Leu Arg Leu Trp
 1               5                  10                  15

<210> SEQ ID NO 12
<211> LENGTH: 18
<212> TYPE: PRT
<213> ORGANISM: Artificial Sequence
<220> FEATURE:
<223> OTHER INFORMATION: Ovispirin-1, chemically synthesized peptide

<400> SEQUENCE: 12

Lys Asn Leu Arg Arg Ile Ile Arg Lys Ile Ile His Ile Ile Lys Lys
 1               5                  10                  15

Tyr Gly

<210> SEQ ID NO 13
<211> LENGTH: 20
<212> TYPE: PRT
<213> ORGANISM: Artificial Sequence
<220> FEATURE:
<223> OTHER INFORMATION: SRP-18, chemically synthesized peptide

<400> SEQUENCE: 13

Gly Arg Leu Lys Arg Met Gly Lys Arg Leu Arg Lys Ile Gln Lys
 1               5                  10                  15

Trp Ala Arg Trp
            20

<210> SEQ ID NO 14
<211> LENGTH: 20
<212> TYPE: PRT
<213> ORGANISM: Artificial Sequence
<220> FEATURE:
<223> OTHER INFORMATION: SRP-19, chemically synthesized peptide

<400> SEQUENCE: 14

Gly Arg Leu Lys Arg Met Gly Glu Arg Leu Lys Arg Lys Ile Gln Lys
 1               5                  10                  15

Trp Ile Arg Trp
            20

<210> SEQ ID NO 15
<211> LENGTH: 20
<212> TYPE: PRT
<213> ORGANISM: Artificial Sequence
<220> FEATURE:
<223> OTHER INFORMATION: SRP-20, chemically synthesized peptide

<400> SEQUENCE: 15

Lys Leu Ile Phe Leu Arg Glu Leu Arg Leu Arg Lys Arg Leu Lys
 1               5                  10                  15

Arg Lys Leu Arg
            20
```

<210> SEQ ID NO 16
<211> LENGTH: 20
<212> TYPE: PRT
<213> ORGANISM: Artificial Sequence
<220> FEATURE:
<223> OTHER INFORMATION: SRP-21, chemically synthesized peptide

<400> SEQUENCE: 16

Gly Arg Leu Lys Arg Met Gly Glu Arg Leu Lys Arg Lys Ile Gln Lys
1               5                   10                  15

Leu Ile Arg Leu
            20

<210> SEQ ID NO 17
<211> LENGTH: 20
<212> TYPE: PRT
<213> ORGANISM: Artificial Sequence
<220> FEATURE:
<223> OTHER INFORMATION: SRP-22, chemically synthesized peptide

<400> SEQUENCE: 17

Gly Arg Leu Lys Arg Leu Gly Glu Arg Leu Lys Arg Lys Ile Gln Lys
1               5                   10                  15

Trp Ile Arg Trp
            20

<210> SEQ ID NO 18
<211> LENGTH: 20
<212> TYPE: PRT
<213> ORGANISM: Artificial Sequence
<220> FEATURE:
<223> OTHER INFORMATION: SRP-23, chemically synthesized peptide

<400> SEQUENCE: 18

Gly Arg Leu Lys Arg Val Gly Glu Arg Leu Lys Arg Lys Ile Gln Lys
1               5                   10                  15

Trp Ile Arg Trp
            20

<210> SEQ ID NO 19
<211> LENGTH: 20
<212> TYPE: PRT
<213> ORGANISM: Artificial Sequence
<220> FEATURE:
<223> OTHER INFORMATION: SRP-24, chemically synthesized peptide

<400> SEQUENCE: 19

Gly Arg Leu Lys Arg Ile Gly Glu Arg Leu Lys Arg Lys Ile Gln Lys
1               5                   10                  15

Trp Ile Arg Trp
            20

<210> SEQ ID NO 20
<211> LENGTH: 15
<212> TYPE: PRT
<213> ORGANISM: Artificial Sequence
<220> FEATURE:
<223> OTHER INFORMATION: SRP-25, chemically synthesized peptide

<400> SEQUENCE: 20

Met Gly Glu Arg Leu Lys Arg Lys Ile Gln Lys Trp Ile Arg Trp
1               5                   10                  15

<210> SEQ ID NO 21
<211> LENGTH: 14

```
<212> TYPE: PRT
<213> ORGANISM: Artificial Sequence
<220> FEATURE:
<223> OTHER INFORMATION: SRP-26, chemically synthesized peptide

<400> SEQUENCE: 21

Gly Glu Arg Leu Lys Arg Lys Ile Gln Lys Trp Ile Arg Trp
1               5                   10

<210> SEQ ID NO 22
<211> LENGTH: 20
<212> TYPE: PRT
<213> ORGANISM: Artificial Sequence
<220> FEATURE:
<223> OTHER INFORMATION: SRP-27, chemically synthesized peptide

<400> SEQUENCE: 22

Gly Arg Leu Lys Arg Leu Gly Glu Arg Leu Lys Arg Lys Ile Gln Lys
1               5                   10                  15

Leu Ile Arg Leu
            20

<210> SEQ ID NO 23
<211> LENGTH: 19
<212> TYPE: PRT
<213> ORGANISM: Artificial Sequence
<220> FEATURE:
<223> OTHER INFORMATION: SRP-28, chemically synthesized peptide

<400> SEQUENCE: 23

Arg Leu Lys Arg Leu Gly Glu Arg Leu Lys Arg Lys Ile Gln Lys Leu
1               5                   10                  15

Ile Arg Leu

<210> SEQ ID NO 24
<211> LENGTH: 18
<212> TYPE: PRT
<213> ORGANISM: Artificial Sequence
<220> FEATURE:
<223> OTHER INFORMATION: SRP-29, chemically synthesized peptide

<400> SEQUENCE: 24

Leu Lys Arg Leu Gly Glu Arg Leu Lys Arg Lys Ile Gln Lys Leu Ile
1               5                   10                  15

Arg Leu

<210> SEQ ID NO 25
<211> LENGTH: 17
<212> TYPE: PRT
<213> ORGANISM: Artificial Sequence
<220> FEATURE:
<223> OTHER INFORMATION: SRP-30, chemically synthesized peptide

<400> SEQUENCE: 25

Lys Arg Leu Gly Glu Arg Leu Lys Arg Lys Ile Gln Lys Leu Ile Arg
1               5                   10                  15

Leu

<210> SEQ ID NO 26
<211> LENGTH: 16
<212> TYPE: PRT
<213> ORGANISM: Artificial Sequence
<220> FEATURE:
<223> OTHER INFORMATION: SRP-31, chemically synthesized peptide

<400> SEQUENCE: 26
```

```
Arg Leu Gly Glu Arg Leu Lys Arg Lys Ile Gln Lys Leu Ile Arg Leu
1               5                   10                  15

<210> SEQ ID NO 27
<211> LENGTH: 20
<212> TYPE: PRT
<213> ORGANISM: Artificial Sequence
<220> FEATURE:
<223> OTHER INFORMATION: SRP-32, chemically synthesized peptide

<400> SEQUENCE: 27

Gly Arg Leu Lys Arg Leu Gly Lys Arg Leu Lys Arg Lys Ile Gln Lys
1               5                   10                  15

Leu Ala Arg Leu
            20

<210> SEQ ID NO 28
<211> LENGTH: 19
<212> TYPE: PRT
<213> ORGANISM: Artificial Sequence
<220> FEATURE:
<223> OTHER INFORMATION: SRP-33, chemically synthesized peptide

<400> SEQUENCE: 28

Arg Leu Lys Arg Leu Gly Glu Arg Leu Lys Arg Lys Ile Gln Lys Leu
1               5                   10                  15

Ile Arg Leu

<210> SEQ ID NO 29
<211> LENGTH: 18
<212> TYPE: PRT
<213> ORGANISM: Artificial Sequence
<220> FEATURE:
<223> OTHER INFORMATION: SRP-34, chemically synthesized peptide

<400> SEQUENCE: 29

Arg Leu Lys Arg Leu Gly Glu Arg Leu Lys Arg Lys Ile Gln Lys Leu
1               5                   10                  15

Ile Arg

<210> SEQ ID NO 30
<211> LENGTH: 17
<212> TYPE: PRT
<213> ORGANISM: Artificial Sequence
<220> FEATURE:
<223> OTHER INFORMATION: SRP-35, chemically synthesized peptide

<400> SEQUENCE: 30

Arg Leu Lys Arg Leu Gly Glu Arg Leu Lys Arg Lys Ile Gln Lys Leu
1               5                   10                  15

Ile

<210> SEQ ID NO 31
<211> LENGTH: 16
<212> TYPE: PRT
<213> ORGANISM: Artificial Sequence
<220> FEATURE:
<223> OTHER INFORMATION: SRP-36, chemically synthesized peptide

<400> SEQUENCE: 31

Arg Leu Lys Arg Leu Gly Glu Arg Leu Lys Arg Lys Ile Gln Lys Leu
1               5                   10                  15
```